United States Patent
Varghese et al.

(10) Patent No.: US 10,478,800 B2
(45) Date of Patent: Nov. 19, 2019

(54) HIGHLY ORDERED TITANIA NANOTUBE ARRAYS FOR PHOSPHOPROTEOMICS

(71) Applicant: University of Houston System, Houston, TX (US)

(72) Inventors: Oomman K. Varghese, Houston, TX (US); Aruna Wijeratne, West Lafayette, IN (US); Maggie Paulose, Houston, TX (US); Ivy Ahiabu, Houston, TX (US); Kenneth D. Greis, Fort Thomas, KY (US); Dharshana Wijesundara, Houston, TX (US); Wei-Kan Chu, Pearland, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 145 days.

(21) Appl. No.: 15/536,758

(22) PCT Filed: Dec. 15, 2015

(86) PCT No.: PCT/US2015/065696
§ 371 (c)(1),
(2) Date: Jun. 16, 2017

(87) PCT Pub. No.: WO2016/100275
PCT Pub. Date: Jun. 23, 2016

(65) Prior Publication Data
US 2018/0015439 A1 Jan. 18, 2018

Related U.S. Application Data

(60) Provisional application No. 62/094,421, filed on Dec. 19, 2014.

(51) Int. Cl.

| | |
|---|---|
| *B01J 20/06* | (2006.01) |
| *C01G 23/047* | (2006.01) |
| *C07K 1/14* | (2006.01) |
| *C07K 1/22* | (2006.01) |
| *G01N 33/68* | (2006.01) |
| *G01N 33/551* | (2006.01) |
| *B01J 20/28* | (2006.01) |
| *B01J 20/282* | (2006.01) |
| *C25D 11/26* | (2006.01) |
| *B01J 20/30* | (2006.01) |
| *G01N 1/40* | (2006.01) |
| *B01D 15/38* | (2006.01) |

(52) U.S. Cl.
CPC ............ *B01J 20/06* (2013.01); *B01J 20/282* (2013.01); *B01J 20/28023* (2013.01); *B01J 20/28083* (2013.01); *B01J 20/28085* (2013.01); *B01J 20/3085* (2013.01); *C01G 23/047* (2013.01); *G01N 1/405* (2013.01); *G01N 33/551* (2013.01); *C01P 2002/72* (2013.01); *C01P 2002/85* (2013.01); *C01P 2004/03* (2013.01); *C01P 2004/13* (2013.01)

(58) Field of Classification Search
None
See application file for complete search history.

(56) References Cited

U.S. PATENT DOCUMENTS

2014/0308728 A1   10/2014   Forstater et al.

OTHER PUBLICATIONS

The International Search Report and Written Opinion issued by the Korean Intellectual Property Office for PCT Application No. PCT/US2015/065696 dated Mar. 2, 2016.
The International Preliminary Report on Patentability issued by the International Bureau of WIPO for PCT Application No. PCT/US2015/065696 dated Jun. 20, 2017.
Min et al., "Tailoring of a TiO2 Nanotube Array-Integrated Portable Microdevice for Efficient On-chip Enrichment and Isotope Labeling of Serum Phosphopeptides", Lab on a Chip, 2013, pp. 3853-3860, vol. 13, No. 19.
Lo et al., "Surface-Assisted Laser Desorption/Ionization Mass Spectrometry on Titania Nanotube Arrays", Journal of the American Society for Mass Spectrometry, 2008, pp. 1014-1020, vol. 19, No. 7.
Yao et al., "Enhanced Osteoblast Functions on Anodized Titanium with Nanotube-like Structures," Journal of Biomedical Materials Research Part A, 2008, pp. 157-166, vol. 85, No. 1.
Li et al., "Novel Fe3O4@TiO2 Core-Shell Microspheres for Selective Enrichment of Phosphopeptides in Phosphoproteome Analysis", Journal of Proteome Research, 2008, pp. 2526-2537, vol. 7, No. 6.
Wijeratne et al., "Phosphopeptide Separation Using Radially ALigned Titania Nanotubes on Titanium Wire", ACS applied Materials & Interfaces, 2015, pp. 11155-11164, vol. 7, No. 21.

*Primary Examiner* — Anand U Desai
(74) *Attorney, Agent, or Firm* — Jackson Walker LLP

(57) ABSTRACT

Titania nanotube arrays are useful for phosphopeptide enrichment and separation. These highly ordered titania nanotube arrays are a low cost and highly effective alternative to the use of liquid chromatography mass spectrometry (LC-MS) methods using meoporous titania beads or particles. The highly ordered $TiO_2$ nanotubes are grown on surfaces coated with Ti metal, or preferably on Ti wires, by methods that preferably include anodic oxidation.

7 Claims, 13 Drawing Sheets
Specification includes a Sequence Listing.

SEQUENCE LISTING

<160> NUMBER OF SEQ ID NOS: 3

<210> SEQ ID NO 1
<211> LENGTH: 14
<212> TYPE: PRT
<213> ORGANISM: Artificial Sequence
<220> FEATURE:
<223> OTHER INFORMATION: Isolated peptide
<220> FEATURE:

```
<221> NAME/KEY: MISC_FEATURE
<222> LOCATION: (10)..(10)
<223> OTHER INFORMATION: Xaa is phosphorylated serine

<400> SEQUENCE: 1

Val Pro Gln Leu Glu Ile Val Pro Asn Xaa Ala Glu Glu Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Isolated peptide
<220> FEATURE:
<221> NAME/KEY: MISC_FEATURE
<222> LOCATION: (12)..(12)
<223> OTHER INFORMATION: Xaa is phosphorylated serine

<400> SEQUENCE: 2

Tyr Lys Val Pro Gln Leu Glu Ile Val Pro Asn Xaa Ala Glu Glu Arg
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Isolated peptide

<400> SEQUENCE: 3

His Gln Gly Leu Pro Gln Glu Val Leu Asn Glu Asn Leu Leu Arg
1               5                   10                  15
```

HIGHLY ORDERED TITANIA NANOTUBE ARRAYS FOR PHOSPHOPROTEOMICS

BACKGROUND

This disclosure pertains to phosphoproteomics or the study of phosphoproteomes in cellular systems and particularly to the use of titania nanotube arrays for separation and evaluation of phosphoproteomes.

Phosphoproteomic analysis offers a unique view of cellular function and regulation in biological systems by providing global measures of a key cellular regulator in the form of protein phosphorylation. Understanding the phosphorylation changes between normal and diseased cells or tissues offers a window into the mechanism of disease and thus potential targets for therapeutic intervention.

Reversible protein phosphorylation is a central regulatory mechanism for normal biological function and cellular homeostasis, while dysregulation of phosphorylation can lead to the initiation and propagation of a variety of diseases. As such, studies aimed at understanding the dynamics of phosphorylation on a global scale in control versus disease conditions have come to the forefront of biological research as the research community attempts to understand the underlying cellular mechanisms of disease with the goal of providing new targets for therapeutic intervention. Currently, methods employing liquid chromatography coupled with tandem mass spectrometry (LC-MS/MS) have become increasingly popular to study protein flux in various cellular systems and their various post translation modifications such as protein phosphorylation. The subset of proteins that are phosphorylated are referred to as phosphoproteomes. For evaluations on proteomes or phosphoproteomes using LC-MS/MS techniques, studies are performed by analyzing their respective peptide solutions generated from various proteolytic digestion strategies. This strategy is referred to as "bottom-up" proteomics. It employs separation of peptides based on their hydrophobic nature using liquid chromatography and analyzing the peptides eluting from LC-columns using mass spectrometry for their identity and quantity. Their respective proteins can then be related to the identified peptides with a variety of available database search algorithms. Such MS based proteomics methods are popular due to (1) high sensitivity, (2) ability to fragment peptides in millisecond time frames, and (3) the ability to identify biochemically modified peptides along with the peptide sequence, thus allowing studies on phosphoproteomes.

The global study of cellular phosphorylation of proteins, commonly called phosphoproteomics, is typically done by first digesting the proteins into specific peptides followed by separation, identification and quantification of the peptides by liquid chromatography coupled with mass spectrometry (LC-MS). The success of these methods is highly dependent on the investigator's ability to effectively separate or enrich the phosphopeptides from non-phosphorylated peptides. This enrichment is required for several reasons: (1) many phosphorylated proteins are in low abundance compared to the total cellular protein and hence, their detection from a complex cellular mixture may be compromised due to the dynamic range of total proteins available; (2) phosphorylation site occupancy on many protein is often at a low stoichiometry (typically <5% but for phosphotyrosine it can be less than 0.1%) thus further diminishing the amount of phosphorylated peptide available for detection; (3) when using electrospray ionization (ESI) mass spectrometry, phosphopeptides are prone to ionization suppression in the positive ion mode when they are analyzed simultaneously with non-phosphorylated peptides. Given these challenges, the research community continually strives to developed ways to enhance the detection and quantification of the phosphopeptides.

For phosphopeptide enrichment, a variety of metal chelation and metal oxide affinity materials have shown great promise with titanium dioxide ($TiO_2$) having emerged as the most popular and widely utilized material. This is due in part to the observed robustness and tolerance of $TiO_2$ towards various reagents, including buffers, salts and detergents that are commonly used in biological protein preparations. This metal oxide, either as spherical porous beads or nanocomposite material in powder form, has demonstrated high efficacy for enrichment via capture of the phosphate group of phosphopeptides in a bridging bidentate configuration between proximal $TiO_2$ groups on the surface of the material. This interaction can be disrupted by high pH elution and the enriched phosphopeptides can be further evaluated by mass spectrometry.

While $TiO_2$ enrichment represents one of the current best available options for phosphopeptide enrichment, it is not without some significant limitations. First, due to the similar chemical structure of peptides containing aspartic or glutamic acids compared to phosphorylated peptides, considerable levels of acidic peptides are also captured by $TiO_2$. This can be partially overcome by including competing additives (e.g. dihydroxybenzoic acid, glycolic acid) in the binding and wash buffers to compete away some of the acidic peptide binding. Secondly, optimization of the amount of $TiO_2$ material needed for a given protein extraction has proven to be challenging based on reports indicating that the efficiency of phosphopeptide capture is highly depending on having the correct ratio of $TiO_2$ to peptides. This means that the optimum ratio must be determined empirically for each sample set thus having a significant impact on the general utility of the method. Another significant challenge is the practical handling of the currently available materials. Typical use of these materials for phosphopeptide enrichments involves preparation of a slurry suspension of the "powdery" material in an appropriate buffer. The material is then packed into micro columns or used as solid phase media in optimized/controlled amounts to capture phosphopeptides. Practical considerations such as weighing out the desired amount of material, transfer of precise amounts from the slurry suspension into each sample and removing the material after eluting the phosphopeptides all add to the variability between experiments.

Finally, the most commonly used material for these studies (Titansphere™ $TiO_2$ Bulk Material-beads, GL Sciences Inc., Japan) is only available in one format as highly porous and spherical beads (FIG. 1) with limited options for further optimization for phosphopeptide enrichment. Controlling the "peptide-to-$TiO_2$ beads ratio" that is decided by the surface area of $TiO_2$ beads has been shown to be a crucial factor in effectively separating the sub-stoichiometric phosphopeptides from the "non-phosphopeptides." That means the amount (in milligrams) of beads utilized has a significant effect on the number of phosphopeptides identified per milligram of protein. However, the porosities or cavities of the beads are irregular in nature (see FIG. 1), indicating these beads provide minimal control of the surface regularity and the surface area.

$TiO_2$ bulk material beads with improved phosphopeptide separation efficiency are yet to be reported. This could be due to the minimal surface manipulation opportunities that this type of $TiO_2$ material provides.

In recent years, titania nanotube arrays grown by anodic oxidation have emerged as a useful material for a wide variety of applications including: gas sensing, dye sensitized solar cells, hydrogen generation by water photoelectrolysis, organic electronics, microfluidics, molecular filtration, drug delivery, and tissue engineering. Being a highly ordered nanostructure with enormous surface area, titania nanotube arrays have also been investigated for phosphopeptide separation. For example, 250 nm long nanotube arrays, fabricated by anodizing titanium foils in aqueous hydrofluoric acid electrolyte, have been reported as a substrate for surface-assisted laser desorption/ionization mass spectroscopy (SALDI MS). A tryptic digest of β-casein was used it was illustrated that phosphopeptides could be selectively trapped on titania nanotubes. In addition, titania thin nanotube array films prepared on glass and patterned in 'S' shape have recently been reported for phosphopeptide enrichment and found to be useful for differential expression analysis of endogenous phosphopeptides between ovarian cancer patients and healthy woman. Despite these different studies, the ability of these materials to serve as alternative and perhaps superior options to the current standard materials used for phosphoproteomic research has not been confirmed or even explored in detail.

What is needed, therefore, is a new material form of porous $TiO_2$ that (1) can readily be immobilized on a given surface (metal or glass), (2) has the ability to be readily quantified in terms of the active surface area, (3) can be manipulated for controlled or variable pore sizes, and most importantly (4) is capable of separating phosphopeptides from their respective "non-phosphorylated" counterparts.

SUMMARY

The present disclosure pertains to highly ordered titania nanotube arrays for use in phosphopeptide separation and enrichment. These arrays have the prominent advantage of having the ability to immobilize $TiO_2$ nano tubes on a given surface with the ability to control the active surface area. In preferred embodiments, the highly ordered titania nanotube arrays are radially aligned titanium dioxide nanotubes (TNTs) on titanium wire (Ti-wire).

The nanotubes can be grown on Ti surfaces using a simple electrochemical process called anodic oxidation that is known for its simplicity and industrial viability. $TiO_2$ nanotubes have potential in a wide variety of applications, such as in sensors (e.g. hydrogen sensors), in dye sensitized solar cells, in hydrogen generation by water photoelectrolysis, in organic electronics, in microfluidics, in molecular filtration, in drug delivery, and in tissue engineering. The unique self-assembled nanoarchitecture has remarkable utility in $CO_2$ and water vapor conversion to hydrocarbon fuels, and also in highly efficient solar cells.

While fabrication of TNT arrays using anodic oxidation is known for its simplicity, cost effectiveness, and industrial viability, the primary advantage of using TNTs on titanium wire for phosphopeptide enrichment is that the surface area can be readily standardized in terms of the length of the wire. One can thus cut the wire into desired lengths to precisely and reproducibly generate the required active surface area for a given phosphopeptide enrichment method. Moreover, the nanotubes grown on wires do not mix into the solution or make colloidal dispersions and hence, in contrast to commonly used Titansphere™ TiO beads, nanotubes-on-wire architecture carries the added benefit of avoiding practical difficulties in separating beads from the solvent medium after elution of the phosphopeptides. In the present disclosure, the efficacy of radially aligned titania nanotubes grown on titanium wire was explored in comparison with the widely used, but expensive Titansphere™ TiO Bulk Material-beads in order to understand if this material could be a low cost alternative for practical use in phosphoproteomic research. It was shown that radially aligned TNTs grown on Ti-wire surfaces are highly suitable for isolating phosphopeptides. Peptides generated from a standard phosphoprotein (α-casein) and mouse liver complex tissue extracts were used. The architecture performed at a comparable level to the standard Titansphere™ $TiO_2$ Bulk Material-beads, while this medium possesses other desirable attributes mentioned above.

An example of preferred embodiments of highly ordered $TiO_2$ nanotubes is shown in FIG. 2. FIG. 2 shows a tilted surface view of the $TiO_2$ nanotube array, revealing the ordered porous architecture. As noted above, FIG. 1 shows SEM images of the Titansphere™ $TiO_2$ Bulk Material-beads, illustrating the spherical morphology associated with the beads and their porosity. FIG. 3 shows a schematic representation of bidentate interaction of phosphopeptide with $TiO_2$. Without wanting to be bound by theory, bidentate coordination of hydroxyl groups to positively polarized Ti(IV) on $TiO_2$ colloidal surface is likely the mode of action that accounts for preferential capture and enrichment of phosphorylated peptides. Previous studies have shown the adsorption of phosphate ions on thin films of colloidal $TiO_2$ using in situ internal reflection infrared spectroscopy. Similar Langmuir binding constants were also observed for phosphate ions and bidentate ligand species such as oxalate and catechol onto colloidal $TiO_2$ at low pH (2.3)—inferring bidentate ligation of phosphorylated peptides on to $TiO_2$ as the mechanism for selective capture of phosphopeptides.

Although the pore openings in commercially available Titansphere™ $TiO_2$ Bulk Material-beads are more or less uniformly distributed, the pore size (depth and diameter) is randomly distributed, which limits the opportunities to further optimize the surface area to enhance phosphopeptide enrichment. In contrast, TNTs on Ti wire are highly ordered, with definite pore size and distribution as evident from the SEM images in FIGS. 3-5. The ability to readily control both the length and porosity of TNTs make them useful for further improving how phosphopeptide enrichment is performed in phosphoproteomics profiling workflows. Although titania nanotubes can be grown on various substrates such as titanium, glass, and silicon having different shapes, the practically useful substrates and architectures are those that provide robustness in phosphopeptide enrichment and ease in determining and optimizing the surface area for effective phosphoproteomics profiling. Radially aligned titania nanotubes grown on wire is such an architecture where surface area of nanotubes can be readily standardized in terms of length of the wire so that a user having an idea of the surface area per unit length of the wire can easily cut and use a wire length that provide the desired surface area. Growth of nanotubes on cylindrical shapes such as wires and pipes has been reported, but the utility of these surfaces for phosphopeptide enrichment has not been demonstrated. Thus, the goal of the present study is to provide an insight on the potential of TNTs on Ti-wire as a viable alternative to Titansphere™ $TiO_2$ Bulk Material-beads for phosphopeptide separations.

Accordingly, described herein is a material useful for phosphopeptide separation that comprises highly ordered $TiO_2$ nanotubes grown on Ti metal surfaces. In preferred embodiments, the TNTs are radially aligned on Ti-wire having a variable, optimized length. Anodization of Ti wires per conditions similar to those given below results in the growth of highly ordered nanotubes pointing radially outward from the surface. The highly ordered TiO₂ nanotube array can be immobilized on a surface or made in the faun of a self-standing membrane. In preferred methods of using these nanotube arrays, a sample suspected of containing one or more phosphopeptides is exposed to the nanotube arrays which bind the phosphopeptides and separate them from the sample. The separated phosphopeptides are then released from the nanotube arrays and may be subjected to further analysis and identification using any suitable method such as sequencing and a database search.

DETAILED DESCRIPTION OF PREFERRED EMBODIMENTS

Figure 1:
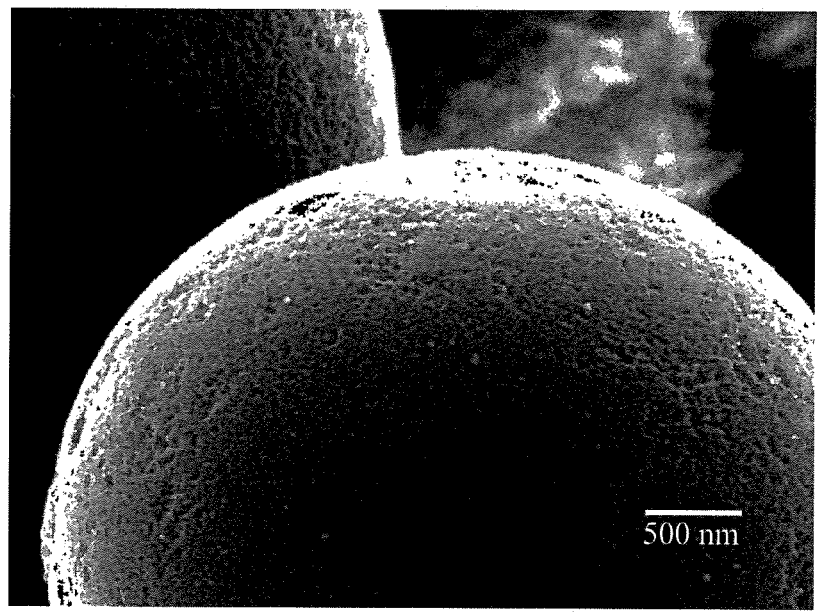
FIG. 1 shows a SEM image of a commercially available mesoporous $TiO_2$ bulk material bead.
Figure 2:
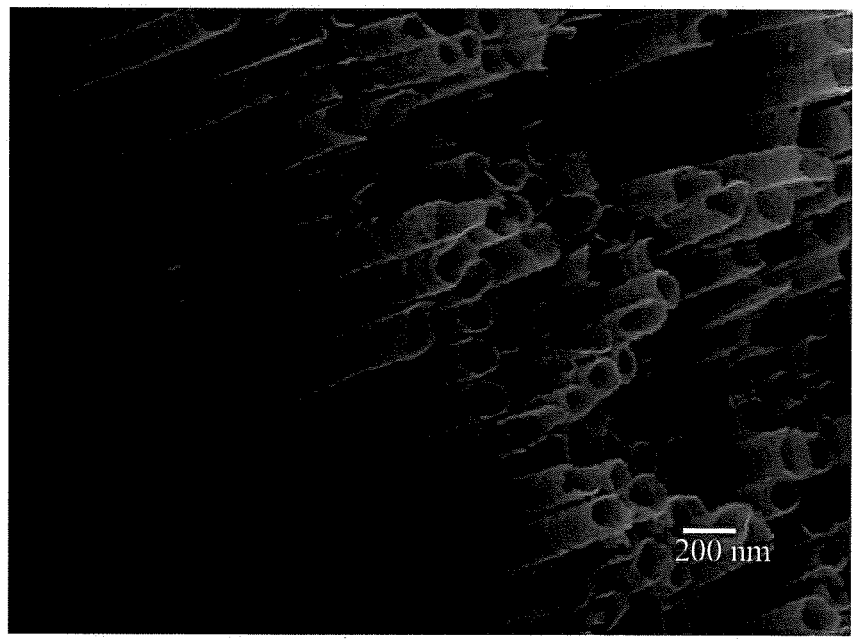
FIG. 2 shows a SEM image of a tilted surface view of an example of a $TiO_2$ nanotube array.
Figure 3:
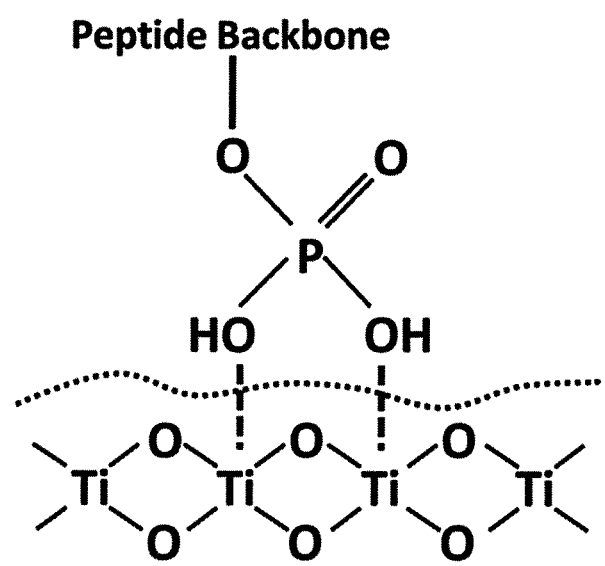
FIG. 3 shows a schematic of bidentate interaction of phosphopeptide with $TiO_2$.

The present disclosure relates to titania nanotube arrays useful for phosphopeptide enrichment and separation. These highly ordered titania nanotube arrays are a low cost and highly effective alternative to the use of liquid chromatography mass spectrometry (LC-MS) methods using meoporous titania beads or particles. These beads or particles are expensive and their irregular pore structure offers very limited opportunities for surface manipulation for any further improvement in performance.

In a preferred embodiment, radially aligned nanotubes were grown by anodic oxidation of titanium wires and their performance was compared to widely used commercially available bulk mesoporous titania beads. Peptides generated from a standard phosphoprotein, α-casein, as well as mouse liver complex tissue extracts were used for the comparison. Example titania nanotubes of length about 10 to about 20 μm, with a pore diameter of about 110 nm and a wall thickness of about 20 nm, demonstrated their capacity to perform on par with the commercially available beads, with further indications that the nanotubes having optimum dimensions could outperform the commercially available phosphopeptide enrichment materials. However, other titania nanotubes having other lengths, pore diameters, and wall thicknesses may also be used, since the optimum dimensions for maximum separation capacity may be outside the ranges recited above. For example, the lengths of the titania nanotubes may range from about 100 nm to about 500 μm, and the pore diameter may range from about 10 nm to about 400 nm.

Thus, the highly porous nature of the commercially available bulk material, which has been effective for phosphopeptide separation, is also achieved in preferred embodiments of the highly ordered $TiO_2$ nanotubes grown on Ti metal surfaces. In preferred examples, $TiO_2$ nanotubes coated on Ti-wires were tested for their capacity for phosphopeptide enrichment, and compared to the phosphopeptide separation capacity of the commercially available bulk material beads as a reference. Ti-wires were chosen for nanotube growth because their quantity and effective surface area for phosphopeptide binding could be simply and appropriately tuned based on the wire length. Ideally, controlled/optimized amounts of $TiO_2$-beads for improved phosphopeptide separation and detection should be used. Thus, instead of controlling the weight of small sample amounts of bulk material beads, the length of Ti-wires bearing titania nanotubes are readily optimized for phosphopeptide separation. Furthermore, the nanotubes coated on Ti wires are immobile, so they do not mix into the solution, hence providing the added benefit of avoiding practical difficulties in separating beads from solvent media. The nanotube array can be immobilized on any suitable solid surface, or it may be utilized without any surface immobilization as a self-stranding membrane. In preferred embodiments, the Ti wire has a diameter from about 0.01 mm to about 1 mm. In additional preferred embodiments, the Ti wire has a diameter of about 0.25 mm.

In additional preferred embodiments, the titania nanotubes are not grown on TI wires. Rather, they are grown inside a container such as a vial. The inside of the container is first coated with titanium, then the titanium is anodized to form the $TiO_2$ nanotubes. Phosphorylated proteins placed inside the container would then attach to the inside of the container.

Experiments demonstrate that the highly ordered titania nanotube arrays grown on Ti surfaces are highly suitable for isolating phosphopeptides. The arrays perform at an appreciable level as compared to bulk material beads while also possessing other desirable attributes. Importantly, the nanotube dimensions can be further varied in length and diameter, thus one can precisely tune the parameters to further optimize their functionality. In addition, the nanotube-on-wire geometry of preferred embodiments facilitates the use of "length of the wire" as a way to easily assess the surface area for phosphopeptide separation experiments and thus eliminate the need for weighing precisely very small amounts of enrichment material or the variability associated with using slurry suspensions of material as in the case of beads. Furthermore, the nanotube arrays may be made available at a much lower cost than the present commercially available materials. The TNTs on Ti wire embodiments are shown to offer similar efficacy for phosphopeptide enrichment compared to the current best approach, while at the same time offering an enhanced ease-of-use. It should be noted that titania nanotubes are not the only nanotubes expected to show these advantages. For example, nanotubes made of oxides of alloys of titanium and zinc oxide may also be useful.

EXAMPLE 1

Materials, Preparation, and Characterization of TiO2 Nanotubes on Ti Wire

Guanidine:hydrogen chloride (GHCl), ammonium bicarbonate (NH4HCO3), Phosphatase inhibitor cocktail 2 (cat. no. P5726), dithiothreitol (DTT), iodoacetamide (IAA), formic acid (HCOOH, FA), triflouroacetic acid (TFA), α-casein from bovine milk (cat. no. C6780, as-casein minimum 70%), acetonitrile (CHROMASOLV®, for HPLC, gradient-grade, >99.9%), water (CHROMASOLV®-Plus, for HPLC), α-cyano-4-hydroxycinnamic acid (CHCA), and glycolic acid were purchased from Sigma-Aldrich (St. Louis, Mo.). For proteomics sample preparation work-flow, deionized water was obtained from an in-house Milli-Q system (Millipore, Bedford, Mass.). All centrifugation steps were completed in an IEC Micromax RF microfuge at 14,600 RCF (Relative Centrifugal Force). Modified trypsin was obtained from Promega (Madison, Wis.). Oligo R3 reversed-phase material was obtained from Applied Biosystems (Foster City, Calif.). For the packing of Oligo R3 reversed phase material, Bio-select extraction columns (reversed phase C4) were obtained from GRACE-VYDAC (W.R. Grace & Co., Deerfield, Ill.). For $TiO_2$-chromatography using "beads", Titansphere $TiO_2$-beads were obtained from GL Sciences Inc. For $TiO_2$-chromatography using "wires", titanium wire of diameter 0.25 mm (99.7% pure) purchased from Sigma Aldrich was used. The electrolyte for anodization of the wire consisted of ammonium fluoride (ACS reagent, 98%, Sigma Aldrich) and ethylene glycol (anhydrous, 99.8%, Sigma Aldrich) and deionized water.

Ammonium hydroxide (trace-metal grade, assay: 20-22% as $NH_3$) was obtained from Fisher Scientific (Hampton, N.J.) for phosphopeptide elution during $TiO_2$-chromatography. Whole mouse liver samples were dounce homogenized in the presence of both protease and phosphatase inhibitor cocktails (Jarrold et al. 2005). Protein concentrations were also determined using NI™ (Non-Interfering™) Protein Assay-Kit purchased from G-BIOSCIENCES.

The Ti wire (diameter ~0.25 mm) was cut into ~25 mm length and degreased by sonication in acetone and then in isopropanol. The degreased wires were again cleaned sequentially in water and Micro-90, isopropanol and acetone and dried with nitrogen gas. Anodization was conducted at room temperature in an electrolyte consisting of 0.3 wt % $NH_4F$, 2 vol % $H_2O$ in Ethylene Glycol. The titanium wire was used as anode and platinum foil as cathode. The anodization was performed for 4 h with 60 V applied between the electrodes. The anodized wires were washed and sonicated in isopropanol to remove debris formed on the surface of the nanotubes during the anodization process. The cleaned samples were annealed at 530° C. in oxygen for 3 h (Varghese et al. 2003).

The morphology of the nanotubes on Ti wire was studied using a field emission scanning electron microscope (FE-SEM; LEO 15125). The crystal structure was identified using a high resolution transmission electron microscope (HRTEM; JEOL 2010) and glancing angle x-ray diffractometer (GAXRD; Rigaku, Smartlab, Cu K-alpha). An array of three nanotube coated wire was used for GAXRD measurements. The incident angle was 0.5°. The x-ray photoelectron spectroscopy (XPS; Physical Electronics, model 5700) was used to determine the composition of the samples.

Figure 4:
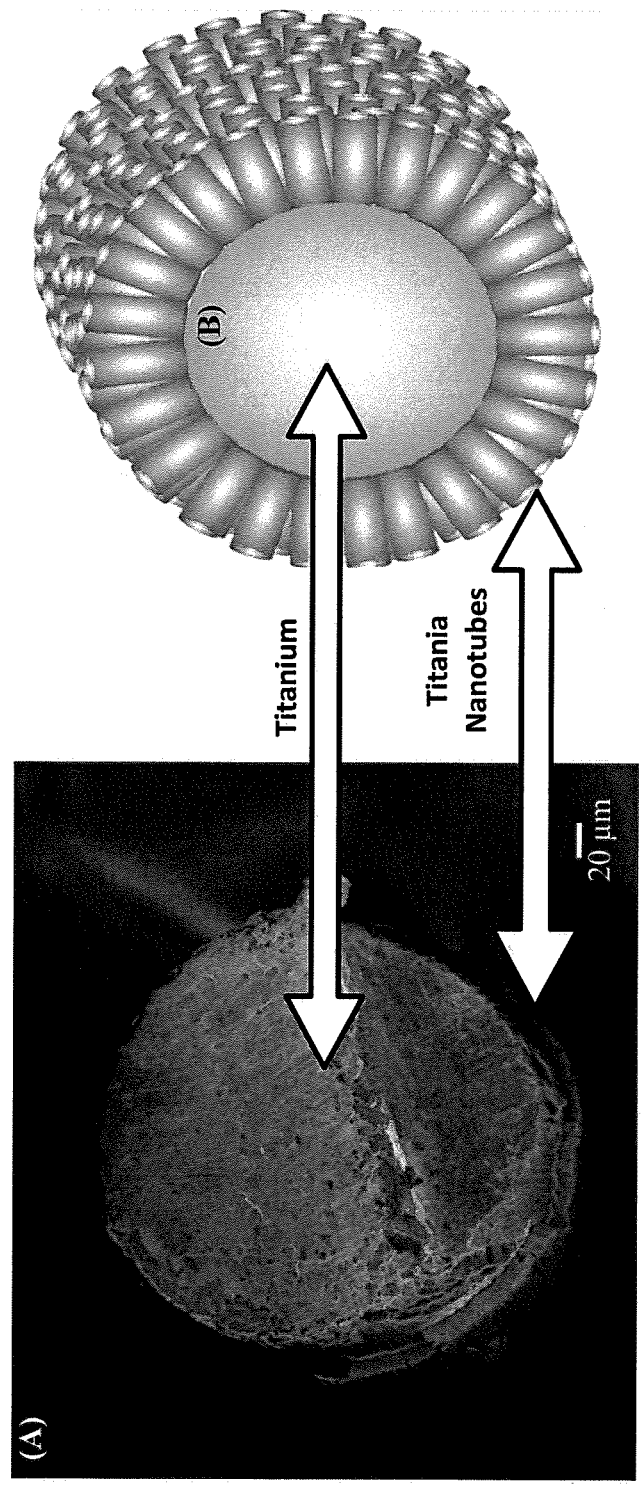
FIG. 4 shows (A) a cross-sectional SEM image of an as-anodized Ti wire sample showing a titania nanotube layer (having a thickness of about 15 μm) covering the titanium wire (having a diameter of about 0.25 mm) and (B) a schematic representation of the orientation of the nanotubes on the surface of the wire substrate.

In order to understand the phosphopeptide separation efficiency of the titania nanotube arrays relative to the most utilized material in the field, $TiO_2$-chromatography was performed in parallel using, (1) the most popularly used and commercially available Titansphere™ $TiO_2$ Bulk Material-beads as a reference material ("Beads") and, 2) Ti-wire pieces grown with $TiO_2$ nanotubes ("Wires"), on a standard phosphoprotein, α-casein and also on mouse liver lysates, to illustrate their phosphopeptide separation capacity, and their applicability in studying complex biological proteomes, respectively. Surfaces of Ti "wire" pieces were modified with $TiO_2$-nanotubes (see FIG. 4), and the wires were particularly chosen so that they could be readily cut into pieces so that effective surface area can be simply be controlled by specific lengths.

Anodization of titanium wires per the conditions given above resulted in the growth of highly ordered nanotubes pointing radially outward from the surface. The SEM image of the cross section of a nanotube-covered Ti wire sample (diameter ~0.25 mm) is given in FIG. 4(A) and an expanded view of the nanotubes on the wire surface is schematically represented in FIG. 4(B). The growth and self-organization of the nanotubes take place during the anodization process and, without wanting to be bound by theory, are believed to be due to the interplay between electric field assisted oxidation of titanium metal and chemical dissolution as well as electric field assisted dissolution of the oxide. An alternate model suggests a stress induced displacement of material rather than field assisted dissolution as responsible for the anodic growth of porous structures. Nevertheless, the nanotubes are grown more or less perpendicular to the substrate surface by consuming the metal and converting into oxide regardless of the growth conditions.

The anodization of titanium in organic electrolytes such as ethylene glycol generally produces anodization debris in the form of particles or nanowires or bunched/broken tubes on the surface of the sample. To remove the debris from the surface of the nanotubes, the wire samples were subjected to ultrasonic agitation at 35 kHz as used normally for other substrates. However, the nanotube films peeled during sonication due to the stress at the oxide/metal interface. The problem was eliminated by performing the ultrasonication at 130 kHz at a reduced power level for 1 to 2 hours. The resulting films were heat treated in oxygen ambient at 530° C. for stoichiometric $TiO_2$ formation and crystallization (Varghese et al. 2003).

Figure 5:
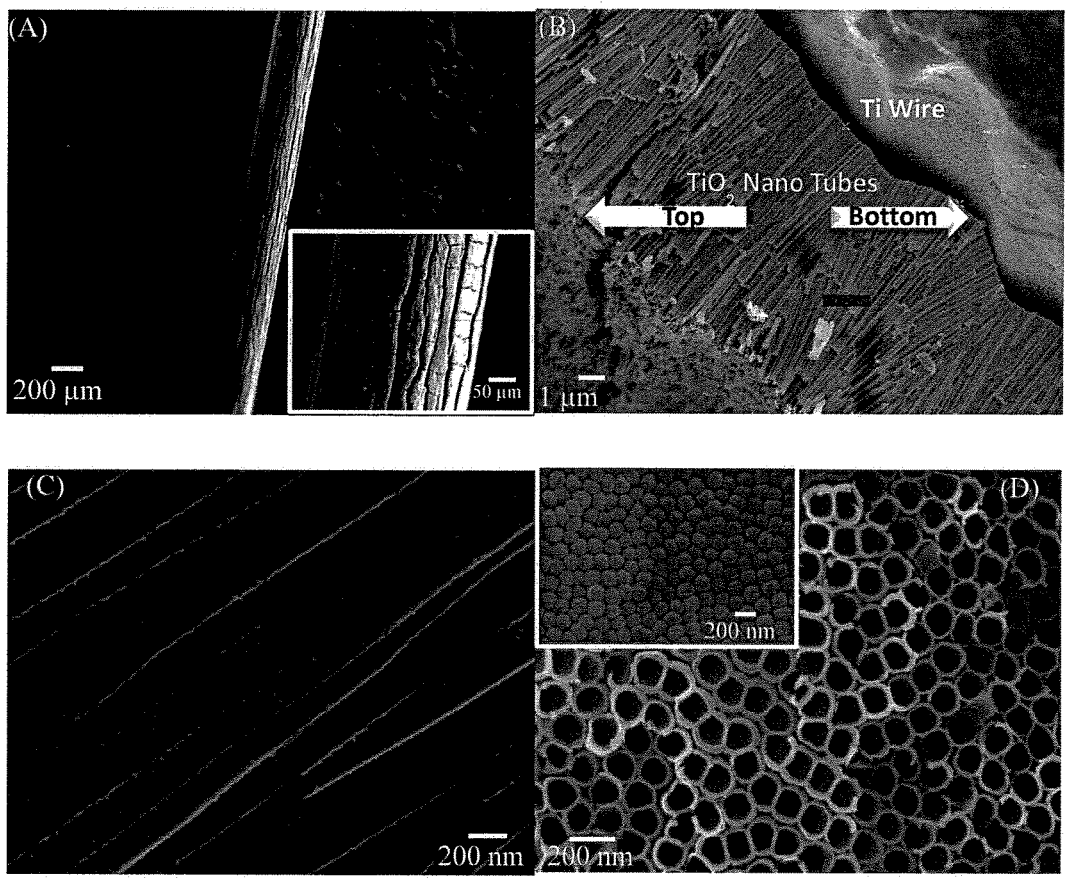
FIG. 5 shows SEM images of (A) a side view of a Ti wire covered with $TiO_2$ nanotubes, with a higher magnification shown in the inset, (B) a side view of nanotubes (having a length of about 10 μm) attached to the Ti wire substrate, (C) a magnified lateral view of the nanotubes, and (D) a view of the top surface of the nanotubes, with a view of the bottom surface of the nanotubes detached from the wire substrate shown in the inset.
Figure 6:
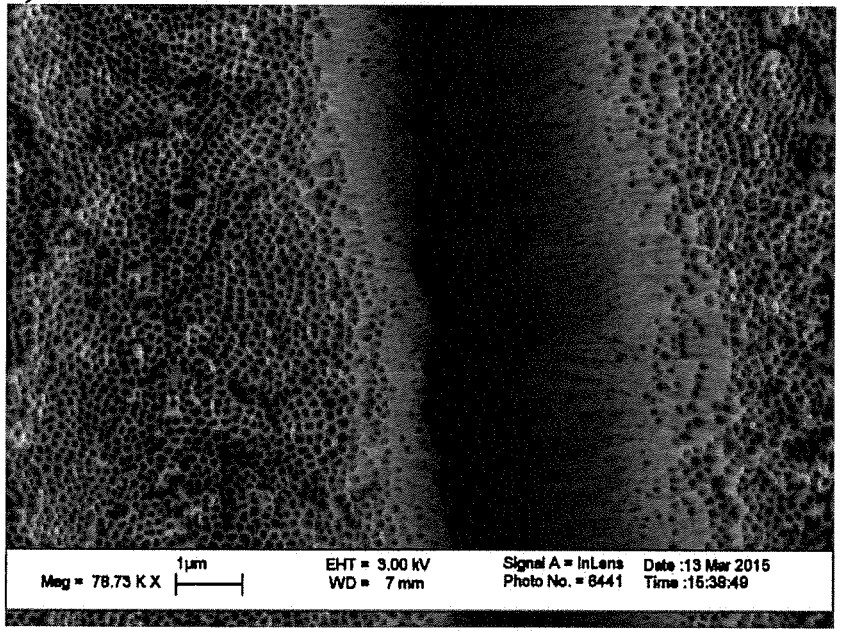
FIG. 6 shows SEM images of nanotubes and a rift caused by stress at (A) a magnification of 78.73 K X and (B) a magnification of 50.00 K X.
Figure 6:
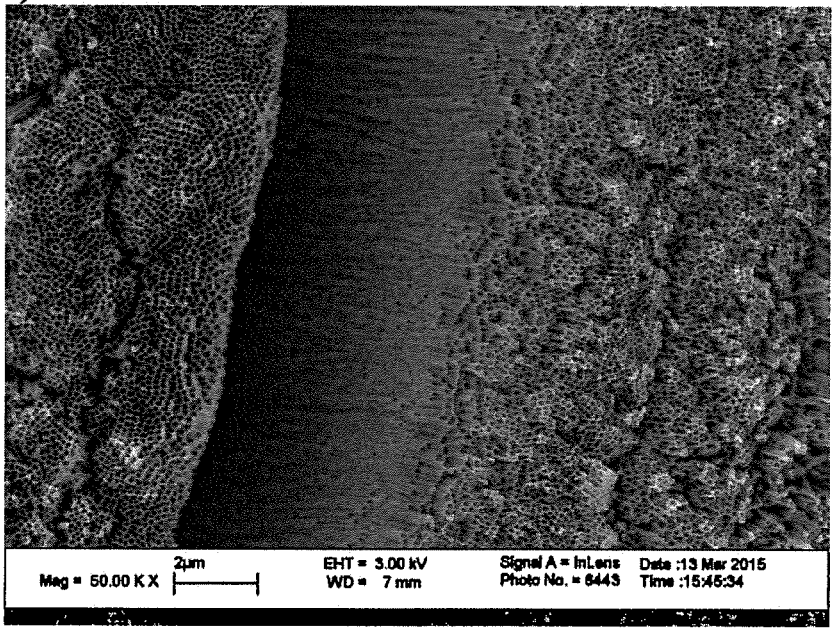

The low magnification SEM images of a heat treated nanotube coated wire sample are shown in FIG. 5(A) and the high magnification images of the nanotubes are given in FIGS. 5(B)-5(D). The nanotube coating appeared like the bark of a tree (see FIG. 5(A) inset) with crevices formed between groups of nanotubes. Studies showed that the crevices were primarily formed during the growth of the nanotubes and not during heat treatment. The images in FIGS. 6(A) and 6(B) give a closer view of the rift between nanotubes. The nanotubes grown using ethylene glycol electrolyte in planar substrates have a more or less hexagonal close packed geometry. Such a configuration cannot be maintained in a cylindrical substrate geometry especially when the radius is small. The lateral stress across the nanotube film increases as the nanotube length increases and as a result partition is formed between nanotubes to relieve the stress. These observations and conclusions are consistent with those previously reported in which cracks were observed in TNT films on wire substrates. Nonetheless, the nanotubes were not detached from the substrate, rather their alignment changed in the partition region. The nanotubes between the crevices were closely packed as evident from the side and top views of the nanotubes given in FIG. 5(B)-5(D). The close packing is maintained from the bottom of the nanotube (see FIG. 5(D) inset) to the top. Nanotubes of length about 10 to 20 µm, pore diameter ~110 nm and wall thickness ~20 nm (measured from SEM images) were used for the study.

Figure 7:
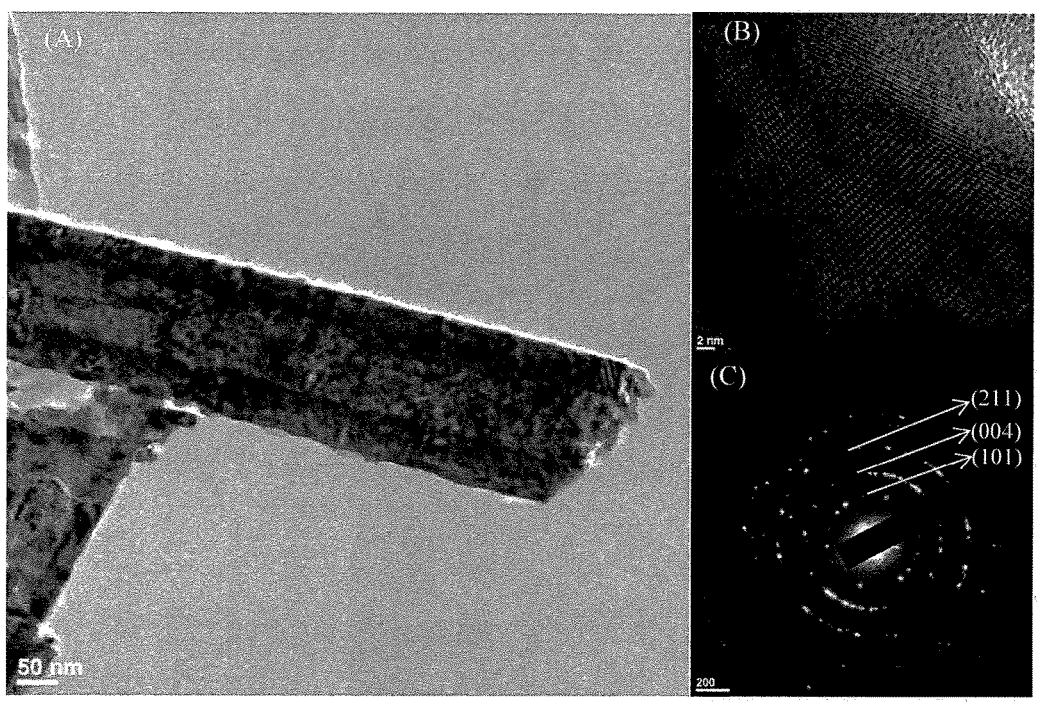
FIG. 7 shows (A) a high resolution transmission electron microscope (HRTEM) image of a nanotube grown on Ti wire, (B) a HRTEM image of the polycrystalline lattice, and (C) selected area diffraction pattern (SAD) from a few nanotubes showing reflections from anatase phase of titania.
Figure 8:
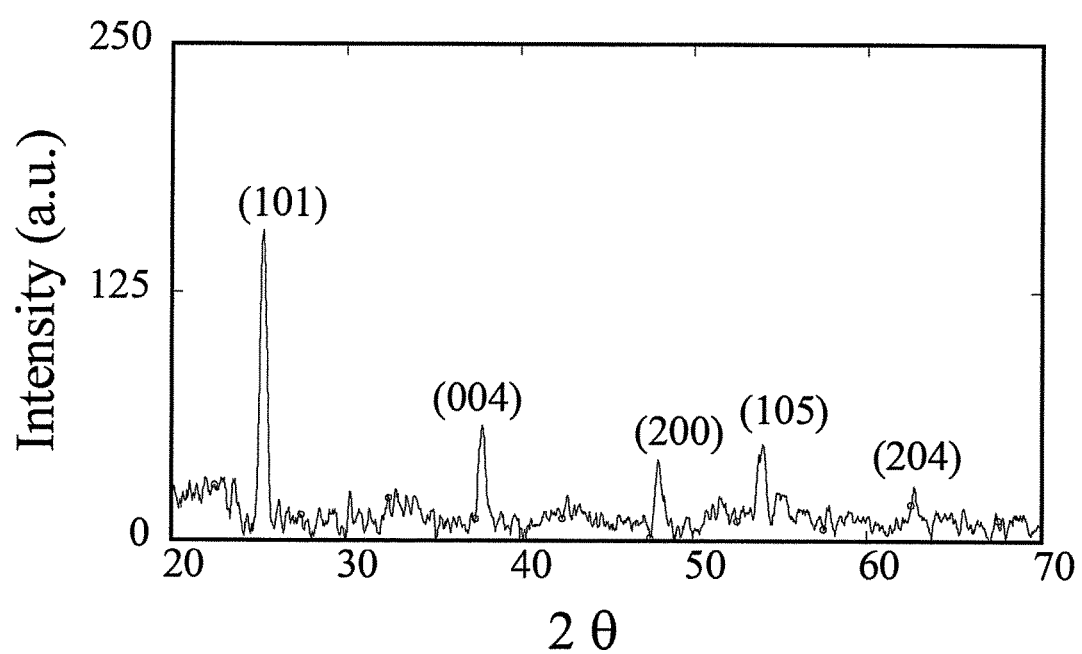
FIG. 8 shows a glancing angle X-ray diffractometer (GAXRD) pattern obtained from a single wire coated with nanotubes.
Figure 9:
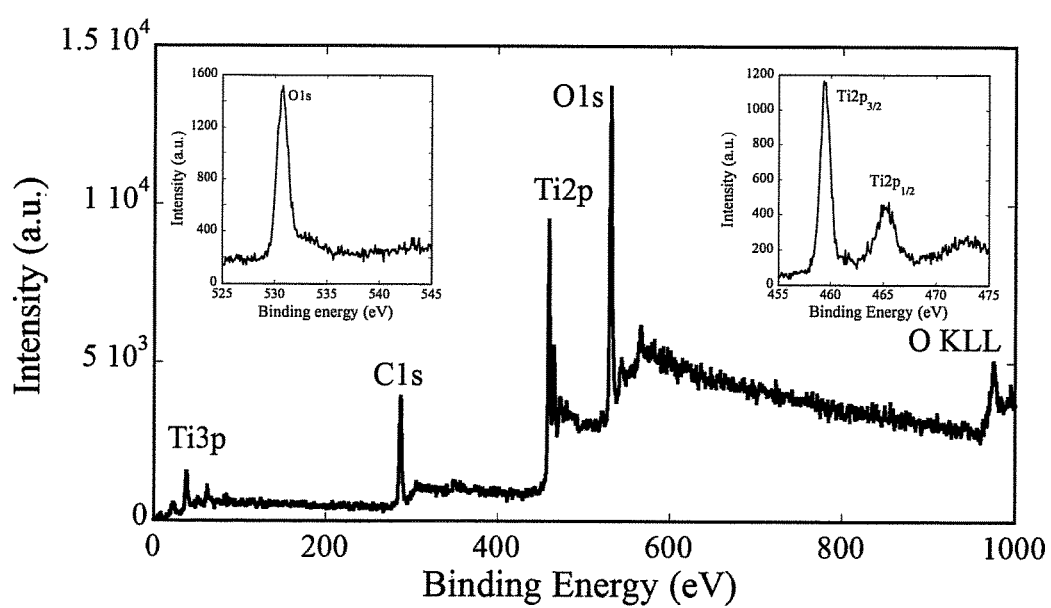
FIG. 9 shows XPS survey spectrum from a titania nanotube film covered Ti wire, with insets showing high resolution scans of the O 1s and Ti 2p peaks.

In order to understand the structure and composition of the heat treated nanotubes on wire substrates, HRTEM, GAXRD and XPS studies were performed. FIG. 7(A) shows the HRTEM images of a nanotube mechanically separated from the wire substrate. The high resolution image of a nanotube region given in FIG. 7(B) shows the polycrystalline lattice. The selected area diffraction pattern (SAD) from a few nanotubes (FIG. 7(C)) revealed reflections from anatase phase of titania. GAXRD patterns obtained from a sample of three nanotube coated wires (FIG. 8) confirmed that the nanotubes consisted of anatase phase of titania. No other phase was found in the samples. This result was further substantiated by XPS studies. The XPS survey spectrum given in FIG. 9 shows the peaks of titanium, oxygen and carbon only. The high resolution scans of O1s and Ti2P peaks are given in the inset. The carbon peak is centered at ~288 eV, which can be attributed to C—O bonds. It is likely that this peak arises from the carbon left on the surface after the burning of the organic electrolyte during heat treatment in oxygen ambient. The stoichiometry of the nanotubes was not estimated as XPS does not provide the composition accurately for nanoporous samples. Nonetheless, significant deviation is not expected from stoichiometry as the pristine oxide samples were heat treated in oxygen ambient. In short, the nanotubes composed of pure titanium dioxide in anatase phase.

EXAMPLE 2

Trypsin Digestion, Desalting of Tryptic Peptides, and Separation of Phosphopeptides using TiO2-Chromatography As reported previously (Wijeratne et al. 2013), 500 µg aliquots of protein were precipitated with 8 volumes of cold acetone (−20° C.) in 1.5 mL Eppendorf tubes. After centrifugation (14,600 RCF, 5 min), supernatants were discarded and pellets were washed three times using −20° C. acetone (100 µL for each wash). Sample tubes were then kept open in a fume-hood for 2 min to ensure any residual acetone vaporization. The pellets were reconstituted in 3 M Guanidine:HCl in 100 mM $NH_4HCO_3$ (90 µL) containing phosphatase inhibitor cocktail (2 µL). The solutions were subsequently reduced with DTT (1 mM final concentration, incubated at 37° C., for 45 min) and then alkylated with iodoacetamide (5.5 mM final concentration, incubated at 37° C., for 30 min). The solutions were finally diluted with $ddH_2O$ to 1 mL before trypsin-based digestion. 100 µg of modified trypsin was dissolved in 300 µL of 0.1 M $NH_4HCO_3$, and 10 µg aliquots were added into each 500 µg protein sample (i.e. 1:50 weight ratio). Samples were then incubated overnight at 37° C., and the digestion was quenched by adding 20 µL of formic acid (to bring the pH of solutions to less than 5). After centrifugation, the supernatants were recovered for further processing. Similarly, 500 µg of bovine α-casein was subjected to trypsin digestion for qualitative comparison of phosphopeptide separation using Titansphere $TiO_2$ Bulk Material-beads ("beads") and Ti-wire surface grown with $TiO_2$ nanotubes ("wires").

Oligo R3 reversed-phase material was dispersed in ACN/$H_2O$/TFA 70/29.9/0.1 (v/v/v) to make a 60 mg/mL slurry as previously described (Wijeratne, et al. 2013; Thingholm, et al. 2008), and divided into 500 µL aliquots each containing 30 mg of Oligo R3 beads in 1.5 mL Eppendorf tubes. The beads prepared for peptide desalting by sequential vortex, spin and removal of the supernatant followed by two wash steps using 200 µL of 0.1% TFA in MilliQ$H_2O$. Peptide solutions were added onto washed Oligo R3 beads and incubated for 30 min at room-temperature using end-over-end rotation. GRACE-VYDAC BIOSELECT-C4 columns (CAT. NO. 214SPE1000) were adapted onto an extraction manifold (Waters Manifold, Mass., USA), washed sequentially with 1) ACN (500 µL), 2) ACN/TFA/$H_2O$ 70/0.1/29.9 (v/v/v, 200 µL), 3) 0.1% TFA (500 µL) and 4) dd $H_2O$ (500 µL), and then packed with peptide-bound Oligo R3 beads by a gentle application of vacuum into the extraction manifold vacuum chamber. Subsequently, the peptide-bound beads were washed with 500 µL dd$H_2O$ and eluted by sequentially passing 200 µL of ACN/TFA/$H_2O$ 90/0.1/9.9 (v/v/v) for one time and then 200 µL of ACN/TFA/$H_2O$ 70/0.1/29.9 (v/v/v) for two times. All elution fractions were collected into 1.5 mL Eppendorf tubes. Prior to $TiO_2$-chromatography, these elution fractions were subjected to vacuum centrifugation for complete dryness.

Phosphopeptide separation of the peptide mixtures was carried out using an optimized strategy adapted from previous reports ((Wijeratne, et al. 2013; Thingholm, et al. 2008; Li, et al. 2009), and was performed in triplicate using identical protein samples for each $TiO_2$-chromatographic method. In using the "beads" for phosphopeptide separation, briefly for each replicate, Titansphere™ TiO$_2$ beads were dispersed in ACN/H$_2$O/TFA 80/15/5 (v/v/v) to make a 100 µg/µL slurry and then divided into 5 µL aliquots each containing 500 µg of TiO$_2$ beads in 0.5 mL Eppendorf tubes. Each vial was subjected to a vortex and spin with supernatants discarded, followed by 2 additional wash steps using 200 µL of 0.1% TFA in MilliQH$_2$O. Dried peptide mixtures (500 µg) were reconstituted in 200 µL of 1 M glycolic acid in ACN/H$_2$O/TFA 80/15/5 (v/v/v), and loaded onto the pre-washed Titansphere TiO$_2$-beads. The peptides were allowed to interact with the TiO$_2$ for 30 min at room temperature using end-over-end rotation. The TiO$_2$ beads were then sequentially washed with 400 µL ACN/H$_2$O/TFA 80/15/5 (v/v/v) with a spin and removal of the supernatant followed by an additional 400 µL wash with the same solvent. Finally the phosphopeptides captured on the TiO$_2$-beads were eluted 1 time with 200 µL of 5% NH$_4$OH. In using the "wires" for phosphopeptide separation, briefly for each replicate, Ti-wire pieces (4×0.5 cm, i.e. 2.0 cm in length) grown with TiO$_2$ nanotubes were placed inside 0.5 mL Eppendorf tubes and subjected to similar washing steps. Following reconstitution of dried peptide mixtures (500 µg) in 200 µL of 1 M glycolic acid in ACN/H$_2$O/TFA 80/15/5 (v/v/v), peptide mixtures were loaded onto the pre-washed Ti-wire pieces grown with TiO$_2$ nanotubes. TiO$_2$ "wires" with loaded peptides were then sequentially washed with 400 µL ACN/H20/TFA 80/15/5 (v/v/v) with a spin and removal of the supernatant followed by an additional 400 µL wash with the same solvent. Finally the phosphopeptides captured on the TiO$_2$-"wires" were also eluted 1 time with 200 µL of 5% NH$_4$OH. The NH$_4$OH elution fractions were dried by vacuum centrifugation prior to nanoLC-MS/MS analysis. For the standard phosphopeptide mixture obtained from α-casein trypsin digestion, 2.5 µL aliquots of the elution fractions were removed from each sample, desalted by ZipTip(C-18µ) as described by the manufacturer (Millipore) and evaluated by Matrix-assisted Laser Desorption Ionization—Time of Flight—Mass Spectrometry (MALDI-TOF-MS) to qualitatively investigate phosphopeptide separation.

MALDI-MS analysis was performed on a 4800 MALDI-TOF/TOF™ instrument (AB Sciex, Foster city, Calif.). Mass spectra were obtained in positive ion reflector mode. MALDI-matrix solution was prepared by dissolving α-cyano-4-hydroxy-cinnamic acid (CHCA, 5 mg) in 10 mM ammonium phosphate (monobasic) in ACN/FA/H$_2$O 60/0.1/39.9 (v/v/v, 1 mL). In order to perform MALDI-MS analyses, desalted (using Oligo R3 reversed phase material or ZipTip™ (C-18 µ)) and isolated peptides in solution (0.5 µL) were mixed with MALDI-matrix solution (1 µL), and spots were placed on a calibrated MALDI plate.

Figure 10:
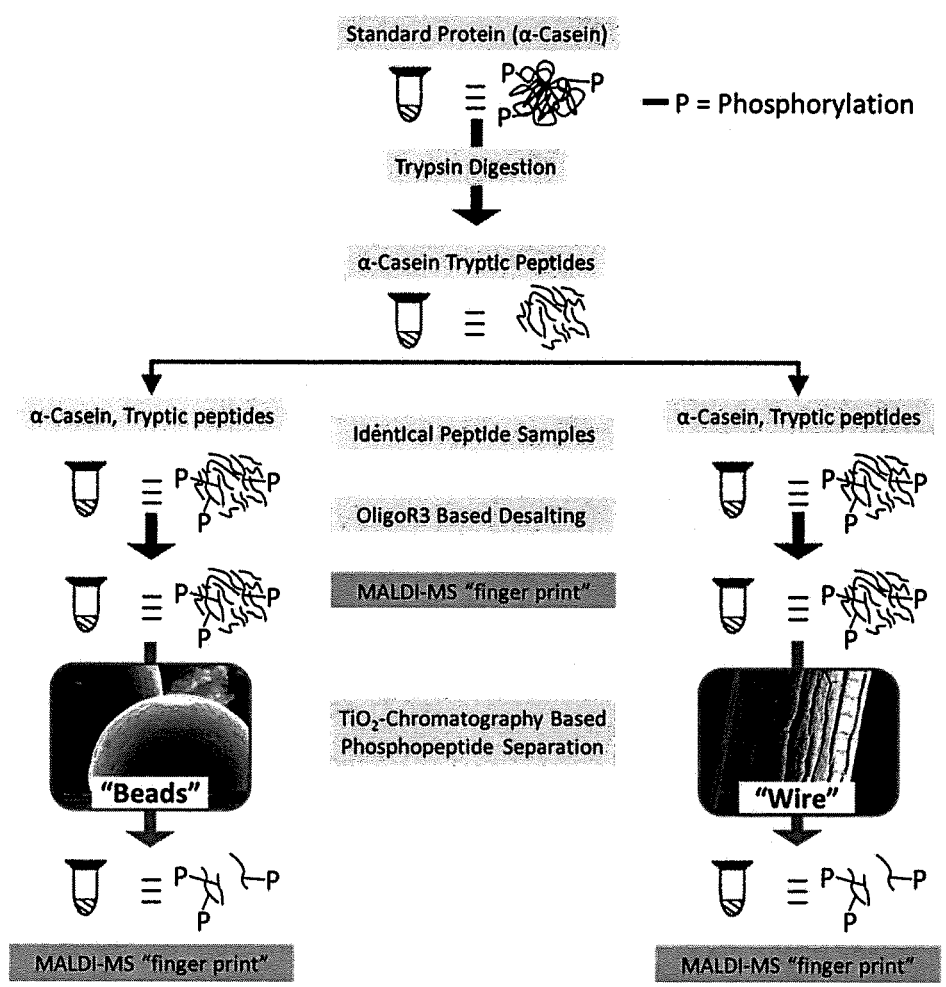
FIG. 10 shows a schematic of an experimental workflow for Matrix assisted laser desorption ionization mass spectrometry (MALDI-MS) analysis of tryptic peptides of a phosphoprotein standard, α-casein, 500 μg was digested using trypsin, to compare phosphopeptide separation of commercially available bulk material beads and examples of a Ti-wire surface grown with $TiO_2$ nanotubes.
Figure 11:
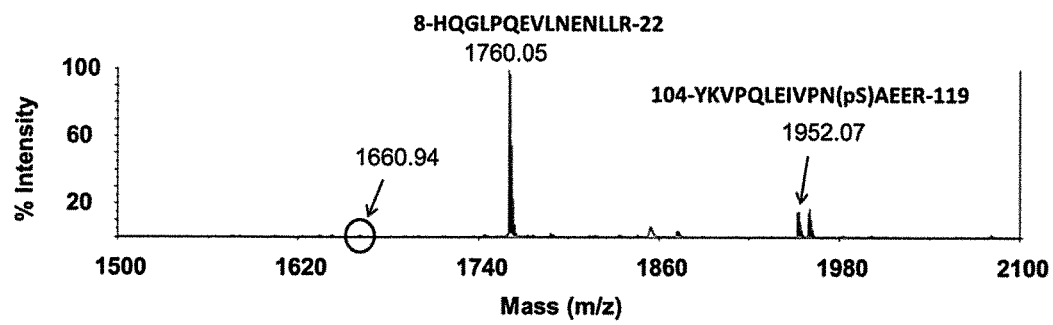
FIG. 11 shows (A) MALDI-mass spectrum of α-casein tryptic peptides, between m/z range 1500-2100, indicating the prominent peptide, 8-HQGLPQEVLNENLLR-22 (SEQ ID NO: 1) at m/z 1760.05, less prominent phosphorylated peptide, 104-YKVPQLEIVPN(pS)AEER-119 (SEQ ID NO: 2) at m/z 1952.07, and infinitesimally small response for the phosphorylated peptide 106-VPQLEIVPN(pS)AEER-119 (SEQ ID NO: 3) at m/z 1660.94; and MALDI-mass spectrum of α-casein tryptic peptides, between m/z range 1500-2100, after phosphopeptide separation using (B) commercially available bulk material beads and (C) an example Ti-wire surface grown with $TiO_2$ nanotubes.
Figure 11:
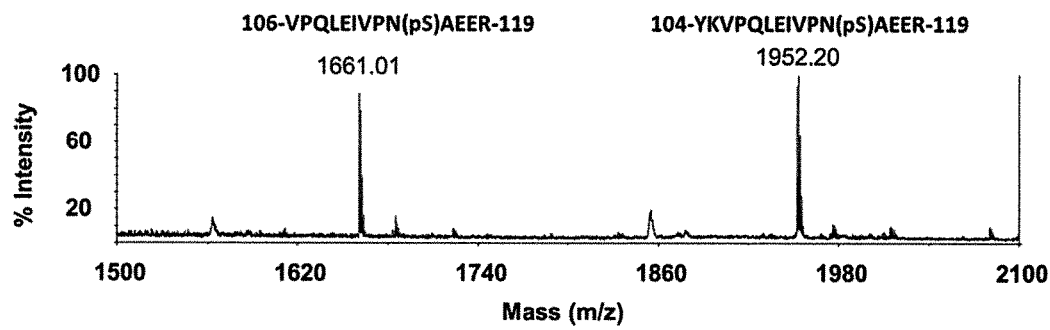
Figure 11:
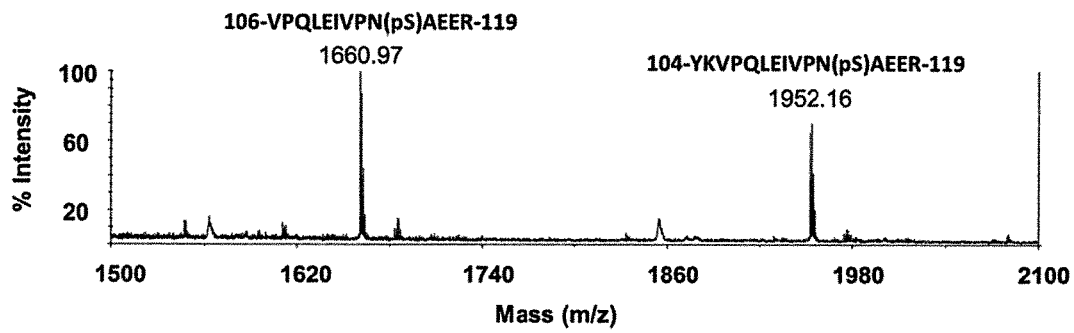

For the qualitative evaluation of phosphopeptide separation capacity of highly ordered TiO$_2$ nanotubes on Ti-Metal "wires" prepared, phosphopeptide separation experiments were first performed using a standard phosphoprotein, α-casein. As illustrated in FIG. 10, tryptic digest from 500 µg of α-casein was first separated into two identical aliquots, i.e. 250 µg each, and subjected to OligoR3 based desalting as described in the methods. Prior to performing TiO$_2$-chromatography, for comparison purposes, a MALDI-mass spectrum (or an MS "finger print") was obtained for desalted α-casein tryptic digest (FIG. 11(A)). During the TiO$_2$-chromatography step, the desalted tryptic digests were pre-treated with both "beads" and "wires". After washing the captured phosphopeptides and eluting them with ammonia solutions as described in methods, MALDI-mass spectra (or MS "fingerprints") were obtained (FIGS. 11(B) from beads and 11(C) from wires). In analyzing the mass spectral regions (m/z 1500 to 2100), after performing TiO$_2$-chromatography either using "beads" or "wires" on α-casein tryptic digests, the phosphopeptides, 106-VPQLEIVPN(pS)AEER-119 (SEQ ID NO: 3) and 104-YKVPQLEIVPN(pS)AEER-119 (SEQ ID NO: 2) represented by m/z values at 1661.01 and 1952.20, are markedly abundant from both TiO$_2$-treatments (FIGS. 11(B) and 11(C)) compare to before TiO$_2$ treatment (FIG. 11(A)). In FIG. 11(A), the most abundant peptide response for the α-casein tryptic peptide before TiO$_2$-treatment is, 8-HQGLPQEVLNENLLR-22 (SEQ ID NO: 1) (m/z 1760.05). The responses at m/z 1660.94 and 1952.07 are either infinitesimally small or relatively low in abundance, respectively. This qualitative illustration demonstrates that TiO$_2$ nanotubes, grown on pieces of Ti-metal wire can be used to enrich phosphopeptides in a comparable manner to TiO$_2$ beads.

EXAMPLE 3

Phosphopeptide Separation Capacity for Phosphoproteomes of Complex Tissue Samples In real biological protein samples or proteomes, it is known that phosphorylation is sub-stoichiometric or very low in abundance. Thus, separation of phosphopeptides from a purified standard phosphoprotein sample like the test case with α-casein may have different dynamics to that of a complex digestion derived from a tissue extract. Hence, the capacity of the highly ordered TiO$_2$ nanotubes in phosphopeptide separation for studying complex phosphoproteomes derived from tissue extracts was also compared with respect to the widely used Titansphere™ TiO$_2$ Bulk Material-beads.

Nano-LC-MS/MS analyses were performed on a TripleTOF™ 5600 (ABSciex, Toronto, ON, Canada) coupled to an Eksigent (Dublin, Calif.) nanoLC.ultra nanoflow system. Dried phosphopeptide samples were reconstituted in FA/H$_2$O 0.1/99.9 (v/v,) and loaded onto IntegraFrit Trap Column (outer diameter of 360 µm, inner diameter of 100, and 25 µm packed bed) from New Objective, Inc. (Woburn, Mass.) at 2 µl/min in FA/H20 0.4/99.2 (v/v) for 10 min to desalt and concentrate the samples. For the chromatographic separation of peptides, the trap-column was switched to align with the analytical column, Acclaim PepMap100 (inner diameter of 75 µm, length of 15 cm, C18 particle sizes of 3 µm and pore sizes of 100 Å) from Dionex-Thermo Fisher Scientific (Sunnyvale, Calif.). The peptides were eluted using a varying mobile phase (MP) gradient from 95% phase A (FA/H$_2$O 0.4/99.6, v/v) to 40% phase B (FA/ACN 0.4/99.6, v/v) for 70 min, from 40% phase B to 85% phase B for 5 min and then keeping the same MP-composition for 5 more minutes at 300 nL/min.

Nano-LC mobile phase was introduced into the mass spectrometer using a NANOSpray® III Source (AB Sciex, Toronto, On, Canada). Ion source gas 1 (GS1) was zero grade air while ion source gas 2 (GS2) and curtain gas (CUR) were both nitrogen. The "gas settings" were kept at 7, 0 and 25 respectively in vendor specified arbitrary units. Interface heater temperature and ion spray voltage was kept at 150° C., and at 2.3 kV. The mass spectrometer method was operated in positive ion mode set to go through 4156 cycles for 90 minutes, where each cycle consisted of one TOF-MS scan (0.25 s accumulation time, in a 400 to 1600 m/z window) followed by twenty information dependent acquisition (IDA) mode MS/MS-scans on the most intense candidate ions selected from initially performed TOF-MS scan during each cycle, having a minimum of 150 counts. Each product ion scan was operated under vender specified high-sensitivity mode with an accumulation time of 0.05 secs and a mass tolerance of 50 mDa. Former MS/MS-subjected candidate ions were excluded for 10 s after its first occurrence, and data were recorded using Analyst®-TF (1.5.1) software.

The nano-LC-MS/MS data (*.wiff file) from the enriched phosphopeptides were analyzed for peptide/protein identification using ProteinPilot™ software (version 4.2, revision 1297) that integrates the Paragon™ algorithm, searched against a SwissProt database of Mus Musculus protein sequences on a local 12-processor server. A custom "sample-type" was selected that specifies variable biological modifications as specified defaults in the ProteinPilot software. The vendor defined phosphorylation emphasis on serine/threonine/tyrosine was also used as a special factor. The resulting *.group files were then used to generate a spreadsheet as a peptide summary report. Only those phosphopeptides identified with a minimum of 95% confidence in identity (calculated by probability algorithms of Protein-Pilot™ software), and phosphorylation as a modification were selected as viable phosphopeptide identifications. Unique phosphopeptides were then selected based on sequence, modifications, and mass to charge ratio (m/z-value) using available software tools on Microsoft Excel. Tools made available by Microsoft Excel were used to determine the number of unique phosphopeptides for each replicate and each $TiO_2$-chromatography method employed.

Figure 12:
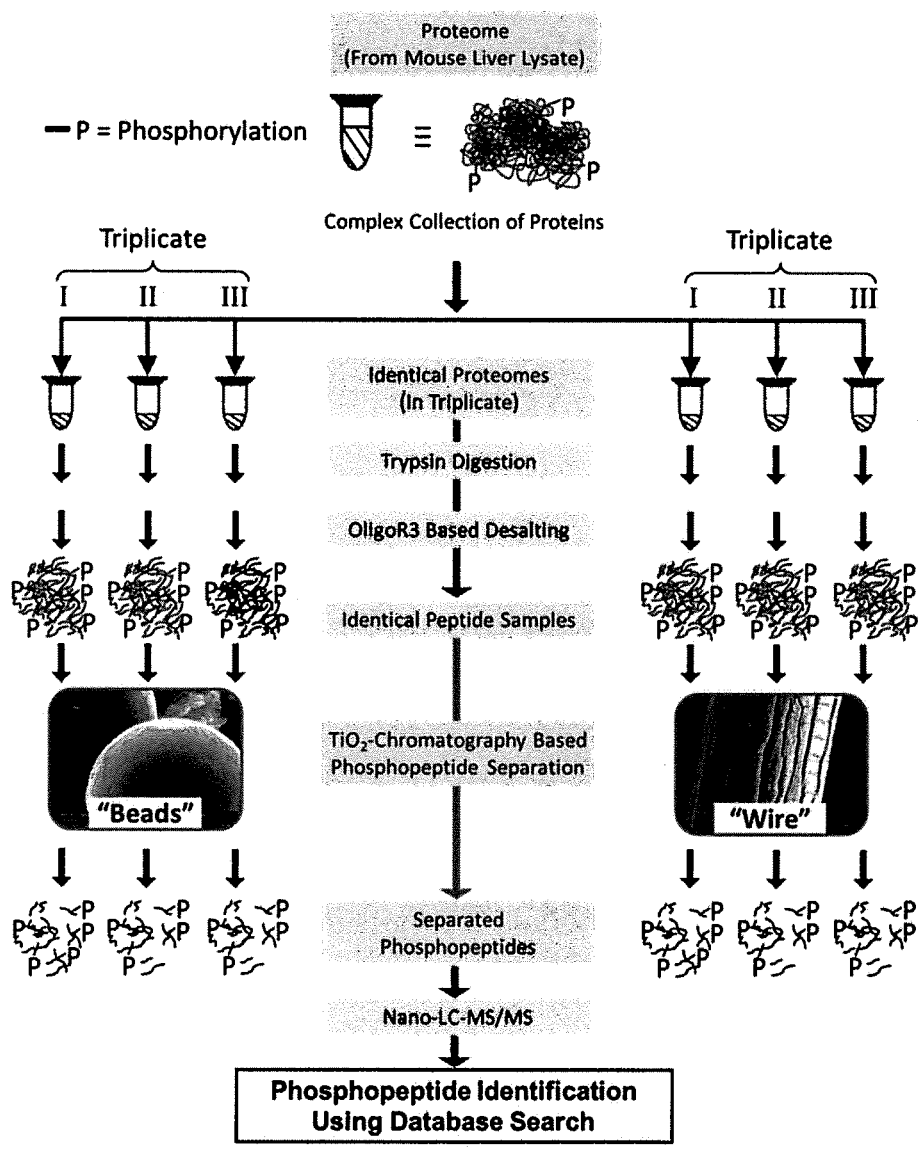
FIG. 12 shows a schematic of an experimental workflow for liquid chromatography-mass spectrometry/tandem mass spectrometry (LC-MS/MS) analysis and identification of mouse liver proteome tryptic peptides to compare phosphopeptide separation capacity of commercially available bulk material beads ("Beads") and examples of Ti-wire surface grown with $TiO_2$ nanotubes ("Wires").

In order to examine the capability of $TiO_2$ nanotubes for phosphopeptide separation in proteomes of complex samples, it was hypothesized that the number of high confidence (>95%) unique phosphopeptides identified using LC-MS/MS and database search algorithms is representative of the phosphopeptide separation capacity in a single phosphopeptide isolation. Hence, an experimental workflow, as depicted in FIG. 12, was implemented and analyzed for unique phosphopeptide identifications. More specifically, from a single pool of mouse liver lysate, as described in the methods, six identical protein solutions (500 μg each) were sequentially subjected for protein precipitation, trypsin digestion, OligoR3 based desalting and phosphopeptide separation using $TiO_2$-chromatography. In performing $TiO_2$-chromatography with "beads", 500 μg equivalents of Titansphere™ TiO Bulk Material-beads were used. For the "wires", 2 cm (0.5 cm×4) of Ti-wire pieces grown with highly ordered $TiO_2$ nanotubes were used. The surface of area of Titansphere™ TiO Bulk Material-beads given by the manufacturer is 100 $m^2$/g and therefore, the surface area of 500 μg beads is about 0.05 $m^2$. The surface area of the nanotubes (pore diameter ~110 nm, wall thickness ~20 nm and length about 15 μm) on a 2 cm long wire of diameter 0.25 mm was calculated using a method reported elsewhere (Varghese, et al. 2009; Shankar, et al. 2007) and is about 0.01 $m^2$. Thus, the Titansphere™ TiO beads used were having surface area about 5 times the surface area of nanotubes. For comparison purposes, triplicate of 1 μg equivalent tryptic digests from mouse liver proteome, were also analyzed using LC-MS/MS, so that "non-phosphopeptide separation" was compared to phosphopeptide separation by either "beads" or "wire" based $TiO_2$-chromatography methods. It was assumed that 1 μg equivalent of tryptic digest analysis in LC-MS from a mouse liver could be used to illustrate the sub-stoichiometric nature of phosphopeptides, and comparison of phosphopeptides identified in such an analysis is illustrative of the separation capacity in using either $TiO_2$-chromatography methodologies. Nevertheless, following all LC-MS/MS analyses/runs of each sample, as described in the methods, each LC-MS/MS run was subjected to database searches to identify high confidence (>95%) unique phosphopeptides. The confidence values were assigned for phosphopeptide identifications from the Paragon probabilistic algorithms used in ProteinPilot search software.

Figure 13:
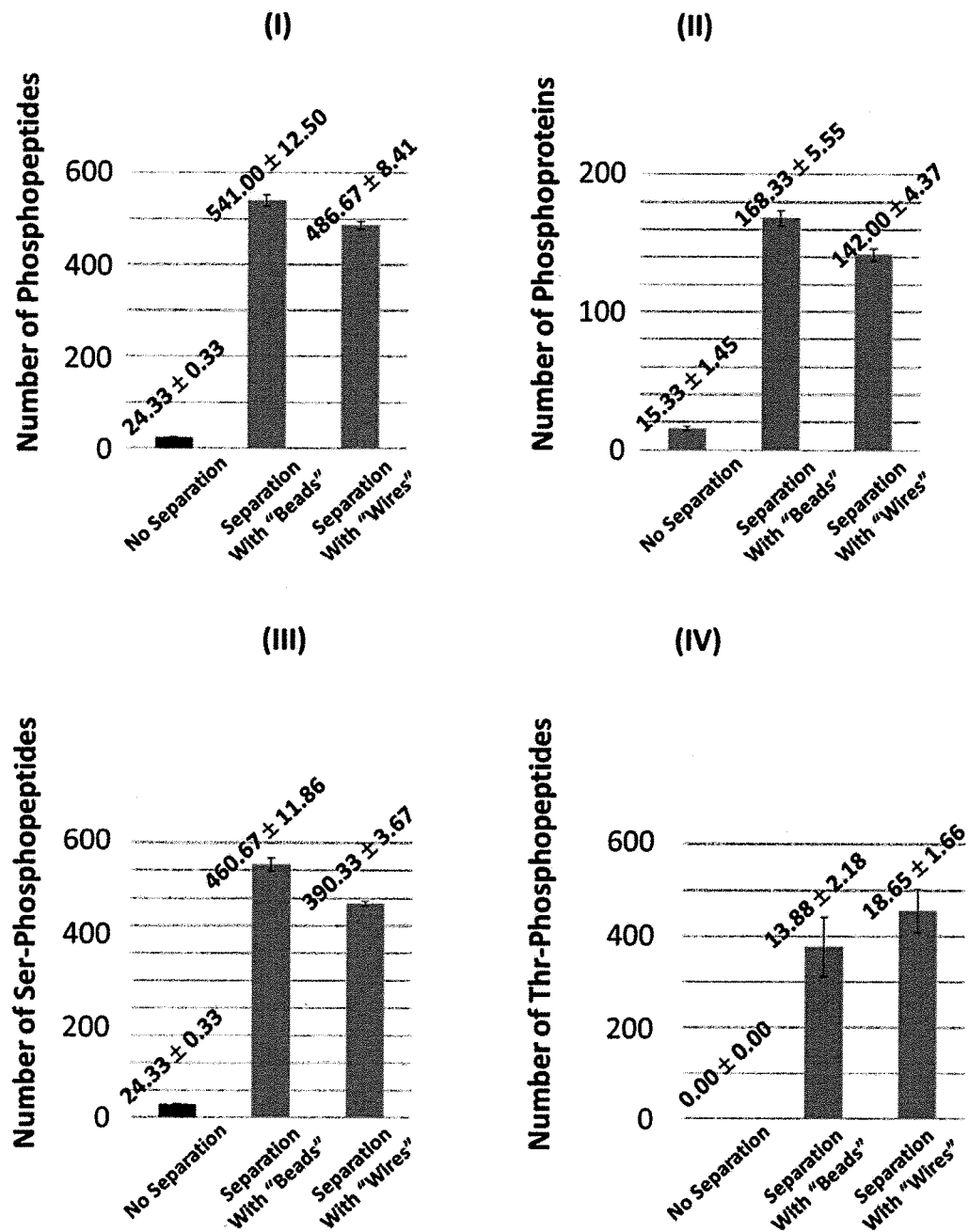
FIG. 13 shows bar-graphs representing, with unique and high confidence (>95%): (I) average number of phosphopeptides, (II) average number of phosphoproteins, (III) average number of Ser-phosphopeptides, and (IV) average number of Thr-phosphopeptides.

The average number of high confidence phosphopeptides (Paragon plus algorithm assigned confidence >95%) identified and their average number of representative phosphoproteins were presented as bar-graphs, FIG. 13 (I & II) for each "beads" and "wire" $TiO_2$-chromatography. In each graph represented in FIG. 13, 1—"No Separation" represents the number of phosphopeptides identified in analyzing 1 μg equivalent of tryptic digest using LC-MS/MS with no $TiO_2$-chromatography performed, 2—"Separation with Beads", and 3—"Separation with Wires" represent number of phosphopeptides identified in analyzing 500 μg equivalent of tryptic digest using LC-MS/MS with $TiO_2$-chromatography performed using, Titansphere™ $TiO_2$ Bulk Material-beads and Ti-wire surface grown with $TiO_2$ nanotubes, respectively. In inspecting FIG. 13 (I & II), it is apparent that, although the surface area is lower, "wires" carry appreciable capacity (average number of phosphopeptides detected, 486.67±8.41) to isolate phosphopeptides in reference to that observed when spherical "beads" are utilized (average number of phosphopeptides detected, 541.00±12.50). In performing $TiO_2$-chromatography for phosphoproteomics studies, it has been well understood that phosphopeptides identified are phosphorylated mostly at serine (Ser or S) and then at threonine (Thr or T) amino acid residues. Thus, the average unique number of high confidence S-phosphopeptides and T-phosphopeptides identified were also plotted as bar-graphs—FIG. 13 (III & IV) for evaluation. It is evident that the "wires" carry a more or less similar capacity to isolate Ser-phosphorylated peptides (390.33±3.67) and Thr-phosphorylated peptides (18.65±1.66), compared to peptides identified with Ser-phosphorylation (460.67±11.86) and Thr-phosphorylation (13.88±2.18) when "beads" are employed. Overall, these results demonstrate that the highly ordered $TiO_2$ nano tubes immobilization on Ti-metal wires carry significant potential as an alternate medium that can be utilized for mass spectrometry based phosphoproteomics workflows.

What is claimed is:

1. A device for isolation of phosphopeptides in a sample, comprising:
    an ordered $TiO_2$ nanotube array comprising ordered $TiO_2$ nanotubes grown on a Ti surface, wherein the nanotubes point outward from the Ti surface, wherein the Ti surface is a Ti wire, and wherein the nanotubes point radially outward from the Ti wire; and
    a container for phosphopeptide isolation, wherein the ordered $TiO_2$ nanotube array is located within the container, and wherein the sample is placed in the container to contact the ordered $TiO_2$ nanotube array.

2. The device of claim 1, wherein the ordered $TiO_2$ nanotubes have a length of about 100 nm to about 500 μm and a pore diameter of about 10 nm to about 400 nm.

3. The device of claim 1, wherein the ordered $TiO_2$ nanotubes have a length of about 10 to about 20 μm, a pore diameter of about 110 nm, and a wall thickness of about 20 nm.

4. The device of claim 1, wherein the Ti wire has a diameter of about 0.01 mm to about 1 mm.

5. The device of claim 1, wherein the Ti wire has a diameter of about 0.25 mm.

6. The device of claim 1, wherein the ordered $TiO_2$ nanotube array is immobilized on the Ti surface.

7. A method for isolation of phosphopeptides in a sample, comprising:
    exposing a sample containing phosphopeptides to the device of claim 1, wherein the sample is placed in the container and wherein the sample contacts the ordered $TiO_2$ nanotube array to produce bound phosphopeptides attached to the ordered $TiO_2$ nanotube array; and
    releasing the bound phosphopeptides from the ordered $TiO_2$ nanotube array to produce isolated phosphopeptides.

* * * * *

UNITED STATES PATENT AND TRADEMARK OFFICE
CERTIFICATE OF CORRECTION

PATENT NO. : 10,478,800 B2
APPLICATION NO. : 15/536758
DATED : November 19, 2019
INVENTOR(S) : Varghese et al.

Page 1 of 1

It is certified that error appears in the above-identified patent and that said Letters Patent is hereby corrected as shown below:

In the Specification

1. In Column 5, Line 4, delete "faun" and insert -- form --, therefor.

2. In Column 7, Line 49, delete "as-casein" and insert -- α-casein --, therefor.

3. In Column 11, Line 27, delete "ACN/H20/TFA" and insert -- $ACN/H_2O/TFA$ --, therefor.

4. In Column 12, Line 41, delete "FA/H20" and insert -- $FA/H_2O$ --, therefor.

Signed and Sealed this
Fifth Day of May, 2020

Andrei Iancu
*Director of the United States Patent and Trademark Office*